US012779007B2

(12) United States Patent
Ross

(10) Patent No.: US 12,779,007 B2
(45) Date of Patent: Nov. 3, 2026

(54) KAVA COMPOSITIONS AND METHODS OF MAKING SAME

(71) Applicant: Jerry Wayne Ross, Santa Monica, CA (US)

(72) Inventor: Jerry Wayne Ross, Santa Monica, CA (US)

( * ) Notice: Subject to any disclaimer, the term of this patent is extended or adjusted under 35 U.S.C. 154(b) by 499 days.

(21) Appl. No.: 18/102,554

(22) Filed: Jan. 27, 2023

(65) Prior Publication Data

US 2023/0248795 A1 Aug. 10, 2023

Related U.S. Application Data

(60) Provisional application No. 63/306,771, filed on Feb. 4, 2022.

(51) Int. Cl.

| | |
|---|---|
| ***A61K 36/67*** | (2006.01) |
| ***A61K 9/16*** | (2006.01) |
| ***A61K 31/366*** | (2006.01) |
| ***A61K 31/4375*** | (2006.01) |
| ***A61K 36/74*** | (2006.01) |
| ***A61K 41/17*** | (2020.01) |

(52) U.S. Cl.

CPC ............ *A61K 36/67* (2013.01); *A61K 9/1688* (2013.01); *A61K 31/366* (2013.01); *A61K 31/4375* (2013.01); *A61K 36/74* (2013.01); *A61K 41/17* (2020.01); *A61K 2236/15* (2013.01); *A61K 2236/17* (2013.01); *A61K 2236/53* (2013.01)

(58) Field of Classification Search

None

See application file for complete search history.

(56) References Cited

U.S. PATENT DOCUMENTS

| | | | | |
|---|---|---|---|---|
| 2005/0069596 | A1 * | 3/2005 | Gow .................... | A61K 31/366 424/734 |
| 2006/0251742 | A1 | 11/2006 | Gow et al. | |
| 2008/0029625 | A1 | 2/2008 | Talton | |
| 2016/0174603 | A1 | 6/2016 | Abayarathna et al. | |
| 2024/0261358 | A1 | 8/2024 | Ross | |

FOREIGN PATENT DOCUMENTS

| | | |
|---|---|---|
| WO | WO-2019/040828 | 2/2019 |
| WO | WO-2021/257586 | 12/2021 |

OTHER PUBLICATIONS

Cinosi, E., et al., Following (the Roots) of Kratom (*Mitragyna speciosa*): The Evolution of an Enhancer from a Traditional Use to Increase Work and Productivity in Southeast Asia to a Recreational Psychoactive Drug in Western Countries, BioMed Research International, vol. 2015, Article ID 968786 (Year: 2015).*

Formerly Normally, Far Exceeded my Expectations Kava & Kratom, Erowid Experience Vaults, Mar. 10, 2012, available at https://www.erowid.org/experiences/exp.php?ID=94846, accessed on Nov. 28, 2023 (Year: 2012).*

Utomo, R.S., et al., Local culture of kratom (*Mitragyna speciosa*) consumption in Kapuas Hulu district, AIP Conf. Proc. 2563, 050026 (2022) (Year: 2022).*

International Search Report and Written Opinion issued in PCT/US2023/012437, mailed May 2, 2023.

Cinosi et al., "Following "the Roots" of Kratom (*Mitragyna speciosa*): The Evolution of an Enhancer from a Traditional Use to Increase Work and Productivity in Southeast Asia to a Recreational Psychoactive Drug in Western Countries," BioMed Research International, 2015; vol. 2015: 11 pages.

FormerlyNormally, "Far Exceeded my Expectations Kava & Kratom," Erowid Experience Vaults, [online], Mar. 2012. Retrieved from the Internet: <URL: https://www.erowid.org/experiences/exp.php?ID=94846>.

Kraken Kratom, Kraken Platinum Liquid Kratom Extract, [online], 5 pages, [retrieved on Mar. 7, 2024]. Retrieved from the Internet: <URL: https://krakenkratom.com/buy-kraken-platinum-liquid-kratom-extract>.

Reddit, "kava kratom mixing," [online], 3 pages, [retrieved on Nov. 28, 2023]. Retrieved from the Internet: <URL: https://www.reddit.com/search/?q=kava+kratom+mixing&type= link>.

Trakulsrichai et al., "Pharmacokinetics of mitragynine in man," Drug Design, Development and Therapy, 2015; 9: pp. 2421-2429.

U.S. Appl. No. 18/213,022, dated Dec. 1, 2023, Office Action issued by the U.S. Patent and Trademark Office.

U.S. Appl. No. 18/213,022, dated Mar. 12, 2024, Final Office Action issued by the U.S. Patent and Trademark Office.

U.S. Appl. No. 18/213,022, dated Sep. 25, 2024, Office Action issued by the U.S. Patent and Trademark Office.

U.S. Appl. No. 18/213,022, dated Mar. 11, 2025, Notice of Allowance issued by the U.S. Patent and Trademark Office.

U.S. Appl. No. 18/639,758, dated Jun. 11, 2024, Office Action issued by the U.S. Patent and Trademark Office.

U.S. Appl. No. 18/639,758, dated Oct. 11, 2024, Final Office Action issued by the U.S. Patent and Trademark Office.

Utomo et al., "Local culture of kratom (*Mitragyna speciosa*) consumption in Kapuas Hulu district," AIP Conf. Proc., 2022; 2563 (1): pp. 050026-1-050026-11.

* cited by examiner

*Primary Examiner* — H. Sarah Park

(74) *Attorney, Agent, or Firm* — Arnall Golden Gregory LLP; John D. Schneible

(57) ABSTRACT

Kava and kratom compositions are described herein along with the methods of producing the same. The description contained herein describes methods for making a purified kava composition that is free or substantially free of flavokavain A and flavokavain B. In some embodiments, the kava composition is formulated as a ready-to-drink beverage. Certain compositions comprise a combination of a kava composition and a kratom composition made in accordance with the methods described herein.

9 Claims, 2 Drawing Sheets

KAVA COMPOSITIONS AND METHODS OF MAKING SAME

CROSS-REFERENCE TO RELATED APPLICATIONS

This is a non-provisional application which claims priority to U.S. Provisional Application No. 63/306,771 filed Feb. 4, 2022, which is incorporated herein by reference in its entirety.

BACKGROUND

Kava, or *Piper methysticum*, is a Pacific Island crop that has demonstrated anesthetic, anti-anxiogenic, and sedative properties, among others, which has suggested its use in nutraceutical and pharmaceutical applications. Compositions of the prior art containing kava, or extracts thereof, however, have been associated with hepatotoxicity. In particular, flavokavain A and flavokavain B, which are present in kava and its extracts, have been associated with hepatotoxicity. The prior art has failed to provide compositions or methods for making compositions comprising kava that addresses these issues. To this end, to fully realize the nutraceutical and pharmaceutical benefits of kava or extracts thereof, the inventors have developed novel methods for preparing kava compositions that are substantially free of flavokavain A and flavokavain B. These novel compositions greatly reduce the risk of hepatotoxicity compared to compositions of the prior art.

Kratom, or *Mitragyna speciosa*, is a tropical tree that has demonstrated a capacity to increase alertness and energy levels, as well as sedative and analgesic properties, among others. To fully realize the nutraceutical and pharmaceutical benefits of kratom or extracts thereof, the inventors have developed novel methods for preparing kratom compositions that exhibit superior and unexpected colloidal properties. These novel compositions greatly improve the stability of kratom compositions in solution, compared to compositions of the prior art.

Owing to the benefits of kava and kratom elucidated by the instant disclosure, the inventors have developed novel compositions comprising one or both components to alleviate, ameliorate, and/or treat pain, conditions, diseases, or disorders associated with neurodivergence, including, but not limited to attention-deficit/hyperactive disorder (ADHD), autism spectrum disorder (ASD), anxiety, dyslexia, dyspraxia, and depression, and/or to improve cognitive ability, focus, mood, relaxation, and/or energy levels.

By providing a kava composition and/or a kratom composition as pharmaceutical agents and/or dietary supplements, therapeutic and nutraceutical benefits can be realized, either individually, collectively, or in conjunction with other pharmaceutical agents and/or dietary supplements.

SUMMARY

Embodiments of the present disclosure relate to novel kava compositions, kratom compositions, or compositions comprising the combination thereof and their use in the amelioration and/or treat of pain and neurodivergent conditions, and their use to improve cognitive ability, focus, mood, relaxation, and/or energy levels.

These and other features, aspects, and advantages of the present embodiments will become understood with reference to the following description and appended claims.

DETAILED DESCRIPTION

Figure 1:
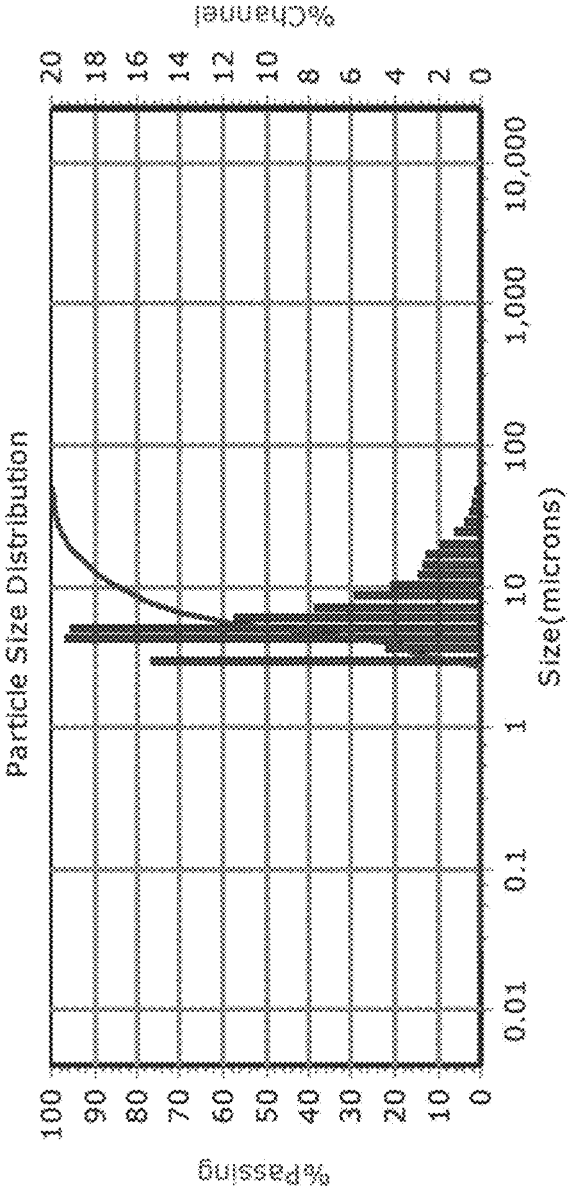
FIG. 1 shows a particle size distribution by number of a kratom composition, as described herein.

Some embodiments provide a composition comprising an amount of kava formulated as a kava composition. Certain kava compositions comprise a pharmaceutically acceptable vehicle, carrier, or diluent. In certain embodiments, a kava composition can comprise ground kava leaves, an extract of kava leaves, ground kava root, an extract of kava root, or a combination thereof. Some embodiments can be formulated to have varying amounts of these constituents.

In certain embodiments, a kava composition, as described herein, may comprise an amount of one or more kavalactones. Kavalactones according to the disclosure include, but are not limited to kavain, dihydrokavain, methysticin, dihydromethysticin, yangonin, and desmethoxyyangonin. When provided in a kava composition, as described herein, the amount of one or more kavalactones in the kava composition may be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1 mg, 2.5 mg, 5 mg, 7.5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or ranges therebetween.

In some embodiments, a kava composition, as described herein, can be formulated to be substantially free of flavokavain A and/or flavokavain B. In certain embodiments, a kava composition, as described herein, can be formulated to contain no flavokavain A and/or flavokavain B. As used herein, when a kava composition is "substantially free" of a flavokavain, the composition comprises at most about 1% by weight of total flavokavain per weight of kava composition, more preferably at most about 0.5% by weight of total flavokavain per weight of kava composition, and most preferably at most about 0.1% by weight of total flavokavain per weight of kava composition. As used herein, and when viewed in the context of the claims and the disclosure, one of skill in the art would immediately envisage the scope and meaning of the phase "substantially free" of flavokavain A and flavokavain B.

Some embodiments provide a composition comprising an amount of kratom formulated as a kratom composition. Certain kratom compositions comprise a pharmaceutically acceptable vehicle, carrier, or diluent. In certain embodiments, a kratom composition can comprise ground kratom leaves, an extract of kratom leaves, ground portions of other parts of a kratom tree, extract of other portions of a kratom tree, or a combination thereof. Some embodiments can be formulated to have varying amounts of these constituents.

In certain embodiments, a kratom composition, as described herein, may comprise an amount of one or more kratom alkaloids. Kratom alkaloids according to the disclosure include, but are not limited to mitragynine, speciociliatine, speciogynine, and paynantheine. When provided in a kratom composition, as described herein, the amount of one or more kratom alkaloids in the composition may be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1 mg, 2.5 mg, 5 mg, 7.5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or ranges therebetween.

In some embodiments, a kratom composition, as described herein, can be formulated to be substantially free of 7-hydroxymitragynine. In certain embodiments, a kratom composition, as described herein, can be formulated to contain no 7-hydroxymitragynine. As used herein, when a kratom composition is "substantially free" of 7-hydroxymitragynine, the composition comprises at most about 0.2% by weight of 7-hydroxymitragynine per weight of total kratom alkaloids, more preferably at most about 0.1% by weight of 7-hydroxymitragynine per weight of total kratom alkaloids, and most preferably at most about 0.05% by weight of 7-hydroxymitragynine per weight of total kratom alkaloids. As used herein, and when viewed in the context of the claims and the disclosure, one of skill in the art would immediately envisage the scope and meaning of the phase "substantially free" of 7-hydroxymitragynine.

Certain embodiments provide a composition comprising an amount of a kava composition, as described herein, and an amount of a kratom composition, as described herein, wherein the amount of a kava composition and the amount of a kratom composition are present in a ratio. In some embodiments, the ratio of the amount of a kava composition to the amount of a kratom composition may be about 1:1. In certain embodiments, the ratio of the amount of a kava composition to the amount of a kratom composition can be within the range of about 50:1 to about 1:50. In this regard, the ratio of the amount of a kava composition to the amount of a kratom composition may be about 50:1, 40:1, 30:1, 20:1, 19:1, 18:1, 17:1, 16:1, 15:1, 14:1, 13:1, 12:1, 11:1, 10:1, 9.5:1, 9:1, 8.5:1, 8:1, 7.5:1, 7:1, 6.5:1, 6:1, 5.5:1, 5:1, 4.5:1, 4:1, 3.5:1, 3:1, 2.5:1, 2:1, 1.5:1, 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, 1:10, 1:11, 1:12, 1:13, 1:14, 1:15, 1:16, 1:17, 1:18, 1:19, 1:20, 1:30, 1:40, 1:50, or any ratio therebetween.

In some embodiments, the ratio of the amount of a kava composition and the amount of a kratom composition present in a composition, as described herein, may be a synergistic ratio. As used herein, a "synergistic ratio" refers to a ratio that elicits an unexpectedly superior pharmacological, physiological, nutritional, or nutraceutical effect in a subject. In some embodiments, the synergistic ratio of the amount of a kava composition to the amount of a kratom composition may be about 10:1. In certain embodiments, the synergistic ratio of the amount of a kava composition to the amount of a kratom composition can be within the range of about 11:1 to about 4.5:1. In this regard, the synergistic ratio of the amount of a kava composition to the amount of a kratom composition may be about 11:1, 10.5:1, 10:1, 9.5:1, 9:1, 8.5:1, 8:1, 7.5:1, 7:1, 6.5:1, 6:1, 5.5:1, 5:1, 4.5:1, or any ratio therebetween. As used herein, an "unexpectedly superior effect" refers to an effect that is at least equal to the combined effects achieved by administration of either component alone, or more preferably, an effect that is greater than the combined effects achieved by administration of either component alone. In certain embodiments, a composition comprising a synergistic ratio, as described herein, may elicit unexpectedly superior effects in improving focus, mood, relaxation, and/or energy levels in a subject. In some embodiments, a composition comprising a synergistic ratio, as described herein, may elicit an unexpectedly superior effect in alleviating, ameliorating or treating pain, and/or conditions, diseases, or disorders associated with neurodivergence, including, but not limited to attention-deficit/hyperactive disorder (ADHD), autism spectrum disorder (ASD), anxiety, dyslexia, dyspraxia, and depression in a subject.

In some embodiments, a kava composition, as described herein, a kratom composition, as described herein, or a composition comprising a kava composition and a kratom composition, as described herein, may further comprise an amount of one or more nutritional supplements. The phrase "nutritional supplement" can refer to a compound that is intended to supplement the diet and bears or contains one or more of the following ingredients: a vitamin, a mineral, an herb or other botanical, an essential amino acid, an essential fatty acid, or any combination of the compounds above. Exemplary nutritional supplements include, but are not limited to linolenic acid, linoleic acid, caffeine, creatine, tryptophan, lysine, methionine, phenylalanine, threonine, valine, leucine, isoleucine, arginine, histidine, retinol (vitamin A), retinal, retinoic acid, carotenoid compounds and derivatives thereof, thiamine (vitamin B1), riboflavin (vitamin B2), niacin (vitamin B3), pantothenic acid (vitamin B5), pyridoxine, pyridoxamine, or pyridoxal (vitamin B6), biotin (vitamin B7) or pharmaceutically acceptable salts thereof, folic acid (vitamin B9) or pharmaceutically acceptable salts thereof, cobalamin (vitamin B12), choline, ascorbic acid or ascorbate (vitamin C) or pharmaceutical salts thereof, a mixture of ergocalciferol and lumisterol (vitamin D1), ergocalciferol (vitamin D2), calciferol (vitamin D3), 22-dihydroergocalciferol (vitamin D4), sitocalciferol (vitamin D5), tocopherols or tocotrienols (vitamin E), naphthoquinoids (vitamin K), coenzyme Q10, chromium (including, chromium polynicotinate, chromium picolinate, chromium acetate, chromium histidinate, chromium nicotinate, chromium chloride, and the like, or any or any pharmaceutically acceptable salts, hydrates, solvates, or mixtures thereof), bromine, cobalt, copper, fluorine, germanium, iodine, iron, magnesium, manganese, molybdenum, potassium, selenium, silicon, zinc, calcium, phosphorous, sodium, sulfur, vanadium, and any combination thereof.

When provided in a kava composition, as described herein, a kratom composition, as described herein, or a composition comprising a kava composition and a kratom composition, as described herein, the amount of one or more nutritional supplements may be about 0.01 μg, 0.1 μg, 1 μg, 10 μg, 50 μg, 100 μg, 200 μg, 300 μg, 400 μg, 500 μg, 600 μg, 700 μg, 800 μg, 900 μg, 1 mg, 2.5 mg, 5 mg, 7.5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, or any range or amount in between any two of the preceding values and any other ranges or amounts disclosed herein.

The exemplary compositions described herein, can, in some embodiments, be administered in the methods described elsewhere herein on an hourly basis, e.g., every one, two, three, four, five, six, seven, eight, nine, ten, eleven, twelve, thirteen, fourteen, fifteen, sixteen, seventeen, eighteen, nineteen, twenty, twenty-one, twenty-two, twenty-three hours, or any interval in between, or on a daily basis, every two days, every three days, every four days, every five days, every six days, every week, every eight days, every nine days, every ten days, every two weeks, every month, or more or less frequently.

In some embodiments, a kava composition, as described herein, a kratom composition, as described herein, or a composition comprising a kava composition and a kratom composition, as described herein, may be formulated for oral administration to a subject. In other embodiments, the compositions disclosed herein can be formulated to be administered to a subject as a spray (such as a nasal spray), buccally, sublingually, or the like.

For oral administration, the compositions disclosed herein can be provided as a solid dosage form or a liquid dosage form. As used herein, a solid dosage form can include, but is not limited to a tablet, a pill, a pellet, a hard capsule, a soft capsule, a gelatin capsule, a plant-based capsule, a liquid-containing capsule, a powder or granule, a dispersible powder or granule, a chewable dosage form, a gelatin dosage form, a dissolvable dosage form, or any other solid dosage form suitable for oral administration. As used herein, a liquid dosage form can include, but is not limited to an aqueous suspension, an oil suspension, an aqueous solution, a non-aqueous solution, an emulsion, a syrup, an elixir, a beverage, a tincture, or any other liquid dosage form suitable for oral administration.

In some embodiments, a composition comprising a kava composition and a kratom composition, as described herein, may utilize mixed modes of dosage forms suitable for oral administration, as described herein. For example, the composition may be formulated as an aqueous suspension, e.g., a ready-to-drink beverage, that comprises a kava composition and a kratom composition formulated as dispersible powders. In certain embodiments, dispersible powder dosage forms of a kava composition and a kratom composition are admixed with one or more nutritional supplements, one or more excipients, or any combination thereof, and upon the addition of an aqueous liquid, produce an aqueous suspension. Such excipients include suspending agents, dispersing or wetting agents, one or more preservatives, one or more coloring agents, one or more flavoring agents, one or more sweetening agents, such as sucrose, xylitol, or saccharin, or any combination thereof.

Compositions intended for oral use can be prepared according to any method known in the art for the manufacture of pharmaceutically acceptable compositions and such compositions may include one or more of the following agents: sweeteners, flavoring agents, coloring agents, coatings, and preservatives. The sweetening and flavoring agents can increase the palatability of the preparation. Tablets containing a kava composition and/or a kratom composition in admixture with non-toxic pharmaceutically acceptable excipients suitable for tablet manufacture are acceptable. Such excipients include inert diluents such as calcium carbonate, sodium carbonate, lactose, calcium phosphate or sodium phosphate; granulating and disintegrating agents, such as corn starch or alginic acid; binding agents such as starch, gelatin, or acacia; and lubricating agents, such as magnesium stearate, stearic acid, or talc. Solid dosage forms such as tablets and capsules can be uncoated or can be coated. Such coatings, for example enteric coatings, may be applied by known techniques to delay disintegration and absorption of the dosage form in the gastrointestinal tract, thereby providing a sustained action over a longer period of time. For example, a time delay material such as glyceryl monostearate or glyceryl distearate alone or with a wax can be provided as a coating.

When a composition, as described herein, is formulated as a hard gelatin-containing capsule or a non-gelatinous capsule a kava composition and/or a kratom composition can be mixed with an inert solid diluent, for example, one or more of calcium carbonate, calcium phosphate, and kaolin.

When a composition, as described herein, is formulated as a soft gelatin capsule a kava composition and/or a kratom composition may be mixed with water or an oil medium, such as one or more of peanut oil, liquid paraffin, and olive oil.

When a composition, as described herein, is formulated as an oil suspension, the suspension can be formulated by suspending a kava composition and/or a kratom composition in a vegetable oil, such as *arachis* oil, olive oil, sesame oil or coconut oil, or in a mineral oil such as liquid paraffin. The oil suspension may contain a thickening agent, such as beeswax, hard paraffin, or acetyl alcohol. Sweetening agents, such as those set forth above, and flavoring agents can be added to provide a palatable oral preparation. These suspensions can be preserved by adding an antioxidant, such as ascorbic acid.

Syrups and elixirs, as described herein, can be formulated to contain with a kava composition and/or a kratom composition with sweetening agents, such as glycerol, xylitol, sorbitol, or sucrose. Syrups and elixirs may also contain a demulcent, a preservative, a flavoring, or a coloring agent, as described herein.

In some embodiments, the compositions, as described herein, may be added to food that is designed for animals. For example, a kava composition and/or a kratom composition may be added to and/or comprise a pet treat or biscuit, for example, a dog biscuit or a cat treat.

In certain embodiments, formulations for oral administration, as described herein, may be provided as a controlled release vehicle. Controlled release vehicles are understood by those of skill in the pharmaceutical sciences, and these aspects can be applied to compositions, as described herein. The technology and products in this art are variably referred to as controlled release, sustained release, prolonged action, depot, repository, delayed action, retarded release, and timed release; the words "controlled release" as used herein is intended to incorporate each of the foregoing technologies.

Numerous controlled release vehicles can include, but are not limited to biodegradable or bioerodable polymers, such as polylactic acid, polyglycolic acid, and regenerated collagen. Controlled release drug delivery devices can include creams, lotions, tablets, capsules, gels, microspheres, liposomes, ocular inserts, minipumps, and other infusion devices, such as pumps and syringes.

Controlled release preparations can be achieved by the use of polymers to form complexes with or absorb kava and/or kratom compositions, as described herein. The controlled delivery can be exercised by selecting appropriate macromolecules such as polyesters, polyamino acids, polyvinylpyrrolidone, ethylenevinyl acetate, methylcellulose, carboxymethylcellulose, hydroxymethylcellulose, and protamine sulfate. The concentration of these macromolecules, as well as the methods of incorporation, are selected to control release of the kava and/or kratom compositions. In aqueous solutions, for example, a kava and/or kratom composition can be encapsulated or microencapsulated to control release of these ingredients.

Controlled release can be taken to mean any of the extended release dosage forms. The following terms may be considered to be examples of terms that are substantially equivalent to controlled release, for the purposes of the present disclosure: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

In some embodiments, compositions formulated for oral administration, as described herein, may be designed to deliver the composition(s) to a subject through absorption in the gastrointestinal tract (oral delivery), under the tongue (sublingual delivery), under the lip (sublabial delivery), or in the cheek (buccal delivery).

In certain embodiments, a kava composition, as described herein, a kratom composition, as described herein, or a composition comprising a kava composition and a kratom composition, as described herein, may be administered to a subject to alleviate, ameliorate, and/or treat pain or conditions, diseases, or disorders associated with neurodivergence, including, but not limited to attention-deficit/hyperactive disorder (ADHD), autism spectrum disorder (ASD), anxiety, dyslexia, dyspraxia, and depression, or any combination of the foregoing. In some embodiments, a kava composition, as described herein, a kratom composition, as described herein, or a composition comprising a kava composition and a kratom composition, as described herein, may be administered to a subject to improve cognitive ability, focus, mood, relaxation, and/or energy levels of the subject.

As used herein, the term "extract" means that the referenced compound can be physically or chemically altered to produce one or more compounds capable of being incorporated into the compositions described herein. For example, an extract can be a non-natural compound that is chemically distinct from that which exists in nature by virtue of subjecting a compound or raw material to human-controlled manufacturing or processing techniques, such as those described herein. In certain instances, an extract can refer to a non-natural composition that has had undesired components removed, thereby producing a compound that has markedly different characteristics from that which exists in nature or that possesses an enlarged function compared to natural compositions. In some instances, a composition described herein can deviate from any natural composition by virtue of being formulated into a non-natural combination of constituents, such as those described herein.

As used herein, the terms "preventing", "treating", "treatment," "alleviating," "ameliorating," and the like are used herein to generally refer to obtaining a desired pharmacological, physiological, nutritional, and/or nutraceutical effects, the scopes and meanings of which will be clear to the skilled artisan based upon the context in which these terms are used. The effect may be prophylactic in terms of preventing or partially preventing a disease, symptom, or condition thereof and/or may be therapeutic in terms of a partial or complete cure of a disease, condition, symptom, or adverse effect attributed to the disease. The term "treatment" as used herein encompasses any treatment of a disease in a mammal, particularly a human, and includes: (a) preventing the disease from occurring in a subject that may be predisposed to the disease but has not yet been diagnosed as having it; (b) inhibiting the disease or arresting its development; or (c) relieving the disease, causing regression of the disease and/or its symptoms, conditions, and co-morbidities. In some embodiments, a composition, as described herein, may be administered to maintain healthy levels of a certain condition or biomarker in a subject, such as for example maintaining a healthy level of mental acuity. As set forth herein, any composition that is administered to prevent, treat, alleviate, or ameliorate any condition, can also be administered to maintain a healthy level of a physiological or biological condition. In certain embodiments, a nutritional supplement is administered to maintain a healthy level of one or more of the conditions disclosed herein. The scope and meaning of "preventing," "treating," "treatment," "alleviating," "ameliorating," and "maintaining healthy levels of" would be immediately envisaged by the skilled artisan when viewing the term in the context of the disclosure and the claims.

As used herein, "identifying," refers to detecting or selecting a subject from a population of potential subjects, for example, to establish that a particular subject possesses certain properties or characteristics. "Identifying" may include, for example, self-identification, self-diagnosis, and diagnosis by a medical professional.

The term "pharmaceutical formulation", "formulation", "composition," and the like can refer to preparations that are in such a form as to permit the biological activity of the active ingredients to be effective, and therefore may be administered to a subject for therapeutic use along with dietary and/or nutritional supplement use. The meaning of these terms will be clear to the skilled artisan based upon the context in which they are used.

A "therapeutically effective amount," as used herein, includes within its meaning, a non-toxic but sufficient amount of a compound active ingredient or composition comprising the same for use in the embodiments disclosed herein to provide the desired therapeutic effect. Similarly, "an amount effective to" or "an effective amount," as used herein, includes within its meaning, a non-toxic but sufficient amount of a compound active ingredient or composition comprising the same to provide the desired effect. A "therapeutically effective amount" or an "effective amount" includes amounts of compounds that would not be achievable through a standard or natural diet, but requires supplementation and dosing, as described herein, to achieve specific, non-natural outcomes as set forth herein, along with expanded utilization of any compounds originating from or derived from natural sources. The exact amount of the active ingredient required will vary from subject to subject depending on factors such as the species being treated, the age and general condition of the subject, the severity of the condition being treated, the particular agent being administered, the weight of the subject, the mode of administration, and so forth. Thus, it may not always be possible to specify an exact "effective amount." However, for any given case, an appropriate "effective amount" may be determined by one of ordinary skill in the art in view of the disclosure contained herein.

As used herein, the term "pharmaceutically acceptable solvent" can refer to water or aqueous buffer solutions that are physiologically compatible, or aqueous solutions containing organic solvents that are physiologically compatible. A non-comprehensive list of pharmaceutically acceptable solvents is provided in U.S. Department of Health & Human Services, Food & Drug Administration, "Guidance for Industry: Q3C Impurities: Residual Solvents," December 1997 or its current issue.

As used herein, the term "bioavailability" refers to the amount of a substance that is absorbed by a subject and ultimately available for biological activity in a subject's tissue and cells.

As used herein, the term "excipient" refers to any compound that is part of a formulation that is not an active ingredient, i.e., one that has no relevant biological activity, and which is added to the formulation to provide specific characteristics to the dosage form, including by way of example, providing protection to the active ingredient from chemical degradation, facilitating release from a dosage form in which it is formed, and so forth.

For the purpose of this disclosure, a warm-blooded animal is a member of the animal kingdom which includes but is not limited to mammals and birds. In certain embodiments described herein, a mammal may, for example but without limitation, be a horse, dog, or cat. The most preferred mammal in view of this application is a human.

A kava composition, as described herein, can be prepared by grinding roots of the *Piper methysticum* plant (raw material), along with other suitable portions of the *Piper methysticum* plant. The step of grinding is not particularly limited and the portions, such as the roots, of the *Piper methysticum* plant can be ground in a mill, including, but not limited to a ball mill, an autogenous mill, a ring and puck mill, a Buhrstone mill, a semi-autogenous mill, a vertical roller mill, a roller mill, and the like. In some embodiments, the portions of the *Piper methysticum* plant can be treated prior to grinding, wherein the treatment may be, for example, drying. In other embodiments, the portions of the *Piper methysticum* plant can be ground using cryogenic grinding.

After the raw material has been ground, it can then be subjected to a chromatographic extraction method, including, but not limited to solid phase extraction (SPE), column chromatography, gel permeation chromatography, and the like. Chromatography can be used to isolate compounds of interest from a wide variety of compounds present in the raw material, and separation may occur by separating compounds with disparate properties, such as moisture content, particles size distributions, polarity, and molecular weight, among others. In certain embodiments, a SPE can be performed using $CO_2$. The chromatography step, as described herein, can be utilized to remove flavokavain A and/or flavokavain B from the raw material.

In embodiments that utilize SPE as the chromatographic extraction method, SPE can provide the raw material dissolved or suspended in a liquid (known as a mobile phase) and achieve separation of components in the mobile phase based on the affinity of components within the mobile phase to a solid through which the mobile phase is passed (known as the stationary phase). The stationary phase and/or mobile phases can be tailored to provide separation between desired and undesired components. Here, the stationary phase and/or mobile phases are designed to separate flavokavain A and/or flavokavain B from other components in the raw material, by retaining flavokavain A and/or flavokavain B on the stationary phase. The portion that passes through the stationary phase (flow-through) is collected and further processed to provide a kava composition, as described herein.

The flow-through can be dried to produce a powder. In some embodiments, the drying step is performed using spray drying. The spray-dried powder may be examined to confirm the absence of flavokavain A and/or flavokavain B and determine the composition of the powder, using known methods of the prior art. After the powder is collected, it can further be treated by grinding, sifting, and/or mixing to achieve desired particle size distribution and material consistency.

After treating the powder, it can be packaged or formulated into formulations as described herein.

A kratom composition, as described herein, can be prepared by grinding leaves, or other suitable portions, of the *Mitragyna speciosa* plant (raw material). The step of grinding is limited to microgrinding methods, such as micronization. Micronization may be performed using a high speed shear mixer, and the conditions used in the high speed shear mixer dictates the particle size distribution of the resulting powder. Micronization, as described herein, produces a kratom powder having a size distribution with a mean diameter of less than about 500 μm (by volume), preferably less than about 100 μm (by volume), and most preferably less than about 50 μm (by volume). In some embodiments, the leaves or other suitable portions of the *Mitragyna speciosa* plant can be treated prior to microgrinding (micronization), wherein the treatment may be, for example, drying. In certain embodiments, the leaves or other suitable portions of the *Mitragyna speciosa* plant can be subjected to irradiation, such as subjecting the leaves or other suitable portions of the *Mitragyna speciosa* plant to ionizing radiation. The ionizing radiation source is not particularly limited and may include, but is not limited to gamma rays, an electron beam, or X-rays. The irradiation step can occur prior to the drying step, after the drying step but before the microgrinding step, or after the microgrinding step, and is preferably performed after the microgrinding step.

As described herein, the methods for preparing a kava composition and/or a kratom composition may provide the compositions with a particle size distribution that confers an unexpectedly improved colloidal stability and/or prevents aggregation of the particles comprising the composition when the particles are provided in solution. By way of example, when a kava composition and/or a kratom composition, made via methods as described herein, are provided as powders in an aqueous suspension, said powders may exhibit a reduced "clumping" of the composition within the suspension, an increased duration of homogeneity of the suspension, an improved ability to reconstitute a homogenous aqueous suspension, or any combination thereof compared to compositions of the prior art.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

EXAMPLES

Example 1

A kratom composition was prepared according to the methods described herein. Kratom leaves were dried. The dried kratom leaves were subjected to micronization using a high speed shear mixer, which resulted in a powder. The kratom powder was irradiated by subjecting the powder to ionizing radiation, as described herein.

Figure 2:
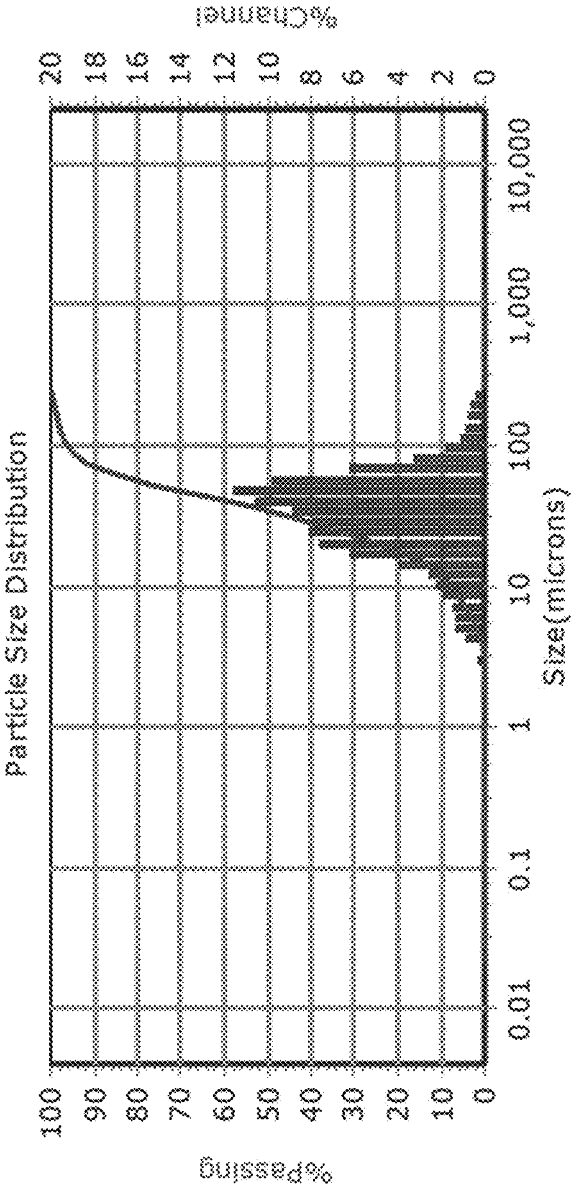
FIG. 2 shows a particle size distribution by volume of a kratom composition, as described herein.

The size distribution of the resultant powder was analyzed using dynamic light scattering (DLS). The reference ASTM B822-20 was used as a guide in an ISO/IEC 17025.2017 facility. The powder demonstrated a mean diameter of the particle size distribution based on number (MN) of 7.0 μm, a mean diameter of the particle size distribution based on area (MA) of 23.3 μm, and a mean diameter of the particle size distribution based on volume of 40.0 μm. Notably, the particle size distribution demonstrated that the kratom powder does not contain particles larger than 55 μm (based on number) or particles larger than 260 μm (based on volume), as shown in FIG. 1 and FIG. 2, respectively.

The sedimentation speed of the resultant powder in aqueous solution was characterized and compared to kratom powders of the prior art. The results demonstrated that the micronized powder, disclosed herein, settles slower and therefore takes longer to result in a sediment in an aqueous solution compared to kratom powders of the prior art. Furthermore, upon forming a sediment in solution the micronized kratom powder disclosed herein was easily reconstituted in solution upon gentle agitation, whereas sediments comprising the kratom powders of the prior art remained as, or returned to, sediments under or after significant agitation.

These results indicate that the micronized kratom powder demonstrates unexpectedly superior results of colloidal properties such as solution homogeneity, stability, and sedimentation time, compared to kratom powders of the prior art.

Example 2

A composition comprising a kava composition and a kratom composition, according to the disclosure was prepared. The kava composition and kratom composition were prepared as dispersible powders, according to the methods disclosed herein. The kava composition was substantially free of flavonoid A and flavonoid B, and the kratom composition was substantially free of 7-hydroxymitragynine. The kava composition and kratom composition powders were provided in an aqueous solution to yield an aqueous suspension. For a 2 oz. aqueous suspension, the following amounts of kavalactones and kratom alkaloids were present. For the kavalactones, the suspension contained 100-200 mg of kavain; 100-200 mg of dihydrokavain; 30-70 mg of methysticin; 30-70 mg of dihydromethysticin; 30-70 mg of yangonin; 30-70 mg of desmethoxyyangonin; no flavokavain A or B; wherein the total kavalactone content was 450-550 mg. For the kratom alkaloids, the suspension contained 30-60 mg of mitragynine; 10-20 mg of speciociliatine; 5-10 mg of speciogynine; 5-10 mg of paynantheine; less than 0.1 mg 7-hydroxymitragynine; wherein the total kratom alkaloid content was 50-100 mg.

Example 3

A randomized, double-blind, placebo-controlled, cross-over clinical trial will be performed using a composition comprising a kava composition and a kratom composition, as described herein, formulated as a capsule. This trial will be undertaken in healthy individuals to assess the effects of the capsules on cognition and self-reported health surveys. Individuals aged 18-55 (male or female) will be eligible to enroll. Kava and kratom compositions will be dosed at levels of 280 mg of kavalactones relative to 28 mg kratom alkaloids, once per day for five days. Alternatively, a placebo arm (containing equivalent amount by weight of 100% microcrystalline cellulose) will be performed where the placebo is taken once per day for five days. Enrollment will be randomized, and individuals will cross-over, but the arm that they are in first will be unknown to participants and clinical trial staff.

Blood samples will be analyzed for content of kavalactones and kratom alkaloids. General hematological assessment will also be performed (including hemoglobin, hematocrit, etc.), as well as clinical chemistry parameters (including basic metabolite panels, liver, and kidney function panels). Vitals will also be measured each day in the clinic.

This study will assess the general safety and tolerability of the inventive formulation in healthy individuals. This will also determine if the inventive formulation improves cognitive scores in a battery of tests.

Additional trials with different patient populations (ADHD, neurodivergent, pain, anxiety, depression) will be carried out in the same manner to determine the effect of the inventive formulation on overall health and well-being.

The invention claimed is:

1. A composition comprising an amount of kratom alkaloids and an amount of kavalactones;

wherein the amount of kratom alkaloids is given by a sum of:
- an amount of mitragynine;
- an amount of speciociliatine;
- an amount of paynantheine;
- an amount of speciogynine; and
- an amount of 7-hydroxymitragynine;

wherein the amount of kavalactones is given by a sum of:
- an amount of kavain;
- an amount of dihydrokavain,
- an amount of methysticin;
- an amount of dihydromethysticin;
- an amount of yangonin; and
- an amount of desmethoxyyangonin;

wherein the amount of speciogynine is between 5 mg and 10 mg;

wherein the amount of 7-hydroxymitragynine is less than 0.1 mg;

wherein the amount of 7-hydroxymitragynine is at most 0.2 wt. % based on the amount of kratom alkaloids;

wherein the amount of kavain is between 100 mg and 200 mg;

wherein the amount of methysticin is between 30 mg and 70 mg; and wherein the amount of desmethoxyyangonin is between 30 mg and 70 mg.

2. The composition of claim 1, wherein the amount of 7-hydroxymitragynine is at most 0.1 wt. % based on the amount of kratom alkaloids.

3. The composition of claim 2, wherein the amount of 7-hydroxymitragynine is at most 0.05 wt. % based on the amount of kratom alkaloids.

4. The composition of claim 1, wherein the amount of speciociliatine is between 10 mg and 20 mg.

5. The composition of claim 1, wherein the amount of kratom alkaloids is between 50 mg and 100 mg.

6. The composition of claim 1, wherein the amount of dihydromethysticin is between 30 mg and 70 mg.

7. The composition of claim 1, wherein the composition is formulated as an aqueous solution.

8. The composition of claim 7, wherein the aqueous solution is a ready-to-drink beverage.

9. The composition of claim 8, wherein the ready-to-drink beverage comprises a volume of 2 oz.

* * * * *